United States Patent [19]

Zeibig

[11] 4,198,711
[45] Apr. 22, 1980

[54] JOINT ENDOPROSTHESIS

[75] Inventor: Anton Zeibig, Ottensoos, Fed. Rep. of Germany

[73] Assignee: Rosenthal Technik AG, Fed. Rep. of Germany

[21] Appl. No.: 808,449

[22] Filed: Jun. 21, 1977

[30] Foreign Application Priority Data

Oct. 14, 1976 [DE] Fed. Rep. of Germany ....... 2646478

[51] Int. Cl.² ............................................. A61F 1/24
[52] U.S. Cl. ...................................... 3/1.91; 3/1.913; 128/92 CA
[58] Field of Search .................................. 3/1.9–1.913; 128/92 CA, 92 C

[56] References Cited

U.S. PATENT DOCUMENTS

| 3,102,536 | 9/1963 | Rose et al. | 3/1.913 X |
| 3,973,278 | 8/1976 | Shersher | 3/1.912 |
| 3,974,527 | 8/1976 | Shersher | 3/1.912 |
| 4,012,795 | 3/1977 | Doore et al. | 3/1.913 X |
| 4,032,994 | 7/1977 | Frey | 3/1.912 |

*Primary Examiner*—Ronald L. Frinks
*Attorney, Agent, or Firm*—Ostrolenk, Faber, Gerb & Soffen

[57] ABSTRACT

A joint endoprosthesis including a pivot body with a radially extending hole; a pin press fit in the hole; a recess extending into the pin from its end in the hole; wedging means for spreading the pin from its end in the hole; wedging means for spreading the pin end in the hole in the body to securely hold the pin.

11 Claims, 2 Drawing Figures

JOINT ENDOPROSTHESIS

FIELD OF THE INVENTION

The invention relates to a bone joint endoprosthesis, especially a hip joint prosthesis, in which a pivot of ductile material is formed on an implantable shaft, and on which a ball-shaped pivot body of brittle material and provided with a radial hole is secured with a press fit.

DESCRIPTION OF THE PRIOR ART

CrCoMo alloys, CrNiMo alloys and also titanium alloys are particularly suitable ductile materials for the shaft and for the pivot of the endoprosthesis, which is usually integral with the shaft. Very pure aluminum oxide is especially approved as the material for the ball-shaped pivot body of the endoprosthesis, by reason of its good resistance to wear and compatibility with tissue.

For example, German OS 24 51 275 discloses a joint endoprosthesis, in which the shaft and pin as an integral component consist of a metal alloy of 15 to 30% Cr, 2 to 37% Ni, 2 to 10% Mo, remainder Co, and the pivot ball consists of a sintered oxide ceramic, which has an $Al_2O_3$ content of more than 99.7%, a density of over 3.90 and a particle size of less than 8 $\mu$m. The pin is conical, with a taper ratio between 1:10 and 1:20. The pin is arranged in a self-locking manner in a corresponding conical bore formed in the pivot body. A firm connection between the pivot body and the pin must be achieved. But, the danger that the pivot body may burst under heavy loading must be avoided. This dual object can be attained most satisfactorily if both the conical pin and the corresponding hole in the pivot body are made with the greatest accuracy.

German OS 21 34 316 describes a hip-joint prosthesis in which the shaft and pin are likewise made integrally, and the ball-shaped pivot body is made of aluminum. The pin and the corresponding radial hole in the pivot body are substantially cylindrical. They have grooves extending parallel to the axis and also in the circumferential direction. Before mounting of the pivot body on the pin, the grooves are filled with cement. The fastening of the pivot on the pin is problematical, because in some cases, the cement is not sufficiently durable to secure the pivot body safely on the pin, while in other cases, the cement holds so firmly that it is not possible to exchange the pivot body for another one, if this should be necessary during another operation in conjunction with an alteration of the associated pivot socket.

The last-mentioned problem may be solved according to British Pat. No. 1,371,335 wherein the ball-shaped pivot body which can be mounted on a conical pin is not solid, but is instead hollowed out around the wall of its radial hole for receiving the pin, so that this wall in the hole in the pivot body forms a kind of sleeve inside the pivot body. This formation is, however, not possible with a pivot body of a brittle material, especially very pure aluminum oxide. With a brittle material, the connection between the sleeve and the usual spherical shell-shaped part of the pivot body would break under high loading.

SUMMARY OF THE INVENTION

The principal object of the invention is to provide a joint endoprosthesis wherein the connection between the pivot body and the pin is sufficiently secure and which, on the other hand, avoids the danger that the pivot body may burst under heavy loading.

This object is realized according to the invention in that the pin has a recess extending in from its free end, which increases the compressibility of the pin in the zone of this end. Thus, the forces acting between the pin and the wall of the hole in the pivot body are smaller than the forces normally present at the end of a solid pin under otherwise similar conditions.

The invention can also be used with cylindrical pins having circular or non-circular, e.g. elliptical, basic surfaces and with prismatic pins, as with frusto-conically shaped pins with circular or non-circular basic surfaces, and with frusto-pyramidal shaped pins. With cylindrical or prismatic pins, press fit seating can be produced by the pin being cooled down to a predetermined temperature before it is inserted in the pivot body. With frusto-conical or pyramidal shaped pins, the press seating arises in the usual manner by the pressing on of the pivot body. In each case, the appropriate size of the recess in the pin can be dimensioned easily so that the forces in the zone of the end of the pin are smaller than the forces arising at the end of a solid pin under otherwise similar conditions.

The invention rests upon the recognition that only in this way can the danger of breakage of the ball-shaped pivot body be decisively reduced. In fact, in contrast to the previous understanding, what increases the danger of breakage is not the tension in the outer end of the radial bore in the pivot body, but the tension in the radially inward zone of the pivot body surrounding the end of the pin. In this annular zone the elastic expansion of the pivot body, which arises within certain limits even with brittle material such as aluminum oxide, is hindered by the spherical segment shaped zone of the pivot body. The latter zone lies beyond the end of the radial bore, in such a way that a concentration of tension arises in the zone around the end of the pin, if, as has hitherto been usual, the pin has over its entire length substantially the same restricted compressibility, which comes from its modulus of elasticity. By providing a recess in the pin according to the invention, the dangerous tension concentration in the zone of the pivot body surrounding the end of the pin is reduced.

A particularly firm seating of the pivot body on the pin, without endangering of the pivot body, occurs if the recess has a shape and size such that the forces acting between the pin and the wall of the hole are approximately constant over the entire length of the press fit. This is true independent of the cross-sectional shape of the pin, and independent of whether the pin tapers towards its end.

In all cases, it is appropriate if the recess in the pin is rounded at its bottom.

In a pin which is rotationally symmetrical, the recess is preferably likewise rotationally symmetrical. If the pin is frusto-conical, the recess can be cylindrical at least over a part of its length. If, in contrast, the pin is cylindrical, then a recess which contracts frusto-conically at least over a part of its length produces a good approximation to the desired uniform distribution of forces over the entire length of the zone of the pivot body surrounding the pin.

The recess in the pin according to the invention can moreover be employed to increase still further the safety against unexpected loosening of the connection between the pivot body and the pin. This happens when the recess receives a wedge member, by which the annular end of the pin can be spread into an enlargement of the hole in the pivot body. The wedge member can, for example, be disc shaped and be clamped between the end of the pin and the bottom of the hole in the pivot body. This clamping action occurs automatically on pressing of the pivot body onto the pin.

However, it is preferred that the wedge body have a threaded extension, which is screwed into a threaded hole of the pin, and which can be tightened up by a tool that is inserted into the wedge body through a prolongation of the hole in the pivot body leading to the wedge body.

BRIEF DESCRIPTION OF THE DRAWINGS

Embodiments of the invention are described with reference to the drawings wherein.

DESCRIPTION OF THE PREFERRED EMBODIMENTS

Figures 1, 2:
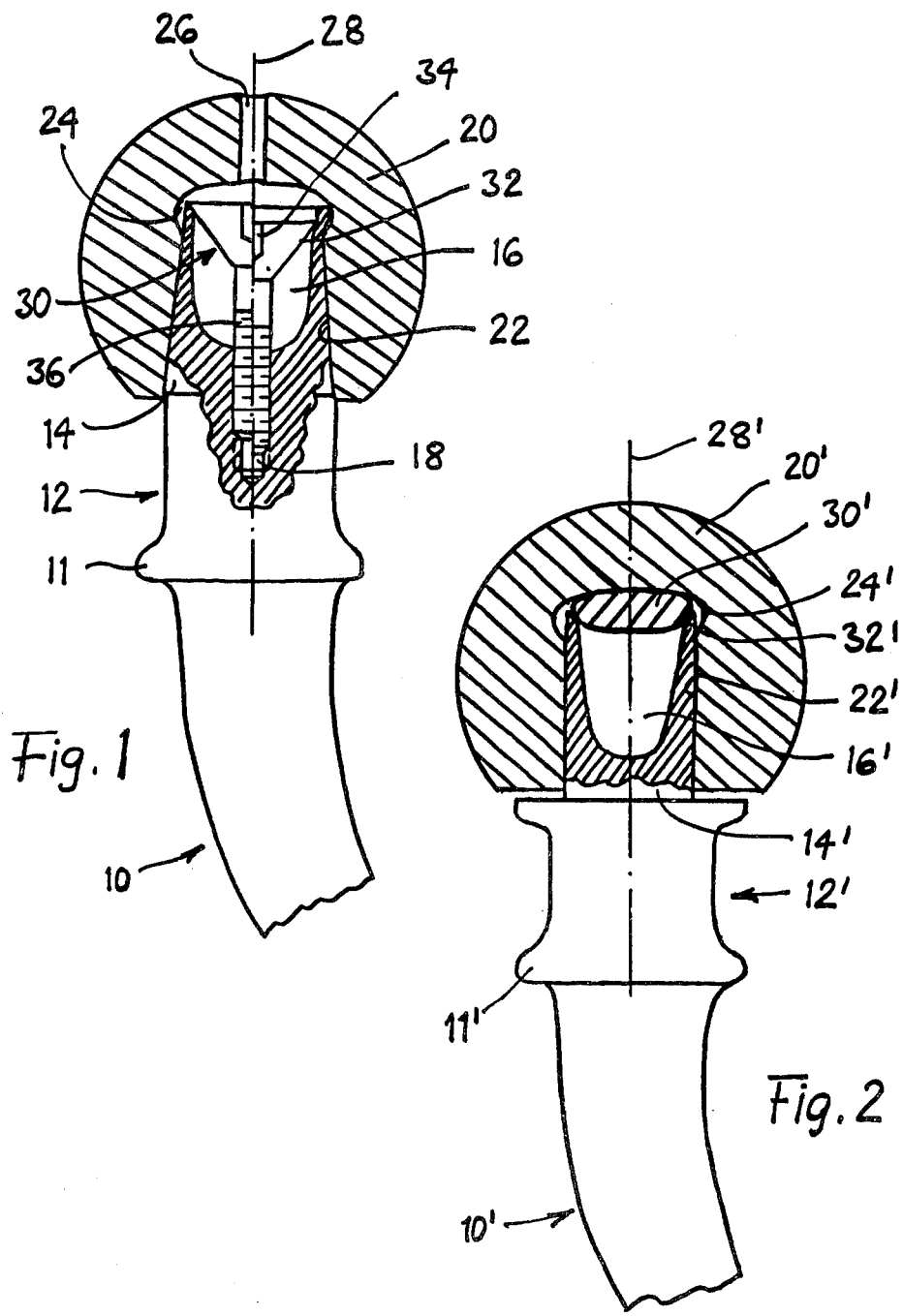
FIG. 1 is an axial cross sectional view through parts of a hip joint prosthesis with a conical connection, wherein at the left half, the wedge device is not fully tightened and at the right half, the wedge device is fully tightened.
FIG. 2 is a corresponding cross sectional view through parts of a hip joint prosthesis provided with a cylindrical connection.

The hip joint prosthesis shown in FIG. 1 has a shaft 10 comprised of a metal alloy, which can be driven into a thigh bone up to a collar 11 formed on the shaft. Above the collar 11 there is a pin 12 which is integral with the shaft 10. The pin is comprised of a ductile metal. The upper part of pin 12 has a frusto-conical external surface 14. A recess 16 extends into the upper part of the pin from its end. The recess 16 is substantially cylindrical, and is coaxial with the frusto-conical external surface 14. The bottom of the recess 16 is rounded and the rounded portion has a relatively large radius. There is a threaded hole 18 in the bottom of the recess 16.

A ball shaped pivot body 20 of very pure aluminum oxide is secured with a press fit onto the pin 12. The material of body 20 is typically brittle. For receiving the pin 12, the pivot body 20 has a radially extending hole 22, which narrows, moving radially inwardly of body 20, with the same cone angle as the external surface 14. Hole 22 has an enlargement 24 at its radially inward end portion. Hole 22 includes a prolongation 26 in the form of a through hole, which extends radially outwardly along the common axis 28 of the pin 12 and the hole 22.

Inside the recess 16 a wedge member 30 is inserted. It has an external cone 32 that narrows moving into recess 16. The wider end of cone 32 engages the upper edge of surface 14 at the entrance to the recess 16. The wedge member 30 has an internal hexagonal cross-section opening 34 on its upper side for receiving a hexagonal key. On its lower side, wedge member 30 has a threaded projection 36, which is screwed into the threaded hole 18 at the bottom of recess 16.

The recess 16 imparts to the pin 12 such an elasticity that the hoop stresses called into play in the pivot body 20 by the press fit of the pin 12 therein are substantially of equal magnitude over the entire length of the hole 22. The enlargement 24 additionally contributes to avoiding stress concentrations in the end zone of the hole 22.

The wedge member 30 can be tightened up with a hexagonal key inserted into the opening 34 through the hole 26 in such a way that, as is shown in the right-hand half of FIG. 1, the annular upper end zone of the pin 12 becomes enlarged and then penetrates into the enlargement 24. This secures pin 12 against unintentional loosening from the pivot body, reinforcing the press fit between the pin 12 and the pivot body 20.

If it should be necessary to release the pivot body 20 during a later operation, then the wedge member 30 can be screwed out upwards beyond the position shown in the left half on FIG. 1, and this would force the pivot body 20 off the pin 12.

The hip joint prosthesis shown in FIG. 2 has numerous features in common with that shown in FIG. 1. The same reference numerals are employed for these features, but marked with a (') indication. The pin 12' on shaft 10' has a cylindrical external surface 14' that mates with pivot 20'. A recess 16', which tapers downwardly frusto-conically is formed in pin 12'. On the outer surface 14' a pivot body 20' is secured with a press fit. For this purpose, body 20' has a radially extending cylindrical hole 22'. The hole 22' terminates at an enlargement 24' inside body 20'.

Positioned between the end of the hole 22' and the annular, downwardly, inwardly tapered end surface of the pin 12' there is a disc-shaped wedge member 30', which has an external inward taper 32' on its lower side. The wedge member 30' is comprised of metal. It can, however, also be made integral with the pivot body 20', and be comprised like body 20, of aluminum oxide.

Upon pressing of the pivot body 20' onto the pin 12', the wedge member 30' is clamped between the pin 12' and the end of the hole 22'. With its external taper 32', the wedge member 30' deflects the annular upper end zone of the pin 12' into the enlargement 24', and thus provides additional securement against unintentional release of the pivot body 20', when the pivot body 20' has been pressed fully onto the pin 12' from the intermediate position shown in FIG. 2.

Although the present invention has been described in connection with a number of preferred embodiments thereof, many variations and modifications will now become apparent to those skilled in the art. It is preferred, therefore, that the present invention be limited not by the specific disclosure herein, but only by the appended claims.

What is claimed is:

1. Joint endoprosthesis, comprising: an implantable shaft; said shaft having an end; a pin formed at said end of said shaft; said pin having a free end; said pin having a recess defined therein by the material of said pin and extending from said pin free end, and by means of said recess in said pin, the radial compressibility of said pin being increased in the zone of said pin through which said recess passes;

a pivot body having a hole defined by the material of said pivot body, and extending into said pivot body; said hole being shaped such that said pivot body is press fit onto and over said pin free end; said pin recess extending a distance along the length of and inside of said hole; said hole being widened at a widened portion thereof at the inner end thereof; said pin free end extends into said widened portion of said hole;

a wedging member, positioned in said hole at said free end of said pin and at said recess for being urged into said recess for spreading said pin at said free end thereof, thereby to secure said pin in said hole in said body; said wedging member being located inside said widened portion of said hole, thereby to enlarge said pin at said free end into said widened portion of said hole.

2. The endoprosthesis according to claim 1, wherein said wedging member is a wedge shaped element having a frusto-conical shape which narrows inwardly moving in the direction into said recess in said pin.

3. The endoprosthesis according to claim 2, wherein said wedging member has a threaded extension therefrom extending through the entire length of said recess and into said pin; said pin having a threaded extension hole at the bottom of said recess into which said threaded extension of said wedge is tightenable, whereby tightening of said threaded extension into said threaded hole in said pin tightens said wedge into said recess and urges said wedge to bias said pin outwardly in said hole of said body at said free end of said pin, means for enabling the rotation of said wedge for tightening said threaded extension into said hole in said pin.

4. The endoprosthesis according to claim 1, wherein said pivot body is generally ball-shaped on its exterior.

5. The endoprosthesis according to claim 1, wherein said pin is comprised of a ductile material.

6. The endoprosthesis according to claim 5, wherein said body is comprised of a brittle material.

7. The endoprosthesis according to claim 4, wherein said hole in said body extends radially of said body.

8. The endoprosthesis according to claim 1, wherein said wedging member is generally disc shaped; said wedging member and said hole being so shaped as to clamp said wedging member against said free end of said pin just inside said recess of said pin for squeezing said wedging member against said pin, thereby to secure said pin in said hole.

9. The endoprosthesis according to claim 8, wherein the side of said wedging member facing inwardly towards said pin recess is rounded and said free end of said pin at the entrance to said recess is correspondingly rounded, thereby to cause said wedging member to urge said free end of said pin outwardly in said hole as said pivot body is clamped in said wedging member.

10. The endoprosthesis according to claim 1, wherein said wedging member is so shaped, with respect to the shape of said recess, that said wedging member applies force to spread said pin only at said pin free end.

11. Joint endoprosthesis, comprising: an implantable shaft; said shaft having an end; a pin formed at said end of said shaft; said pin having a free end; said pin having a recess defined therein by the material of said pin and extending from said pin free end, and by means of said recess in said pin, the radial compressibility of said pin being increased in the zone of said pin through which said recess passes;

a pivot body having a hole defined by the material of said pivot body, and extending into said pivot body; said hole being shaped such that said pivot body is press fit onto and over said pin free end; said pin recess extending a distance along the length of and inside of said pivot body hole; said recess being so shaped and sized that the forces between said pin and said pivot body at said hole are at least approximately constant over the entire length of said press fit connection between said pivot body and said pin;

a wedging member positioned in said hole at said free end of said pin and at said recess for being urged into said recess for spreading said pin at said free end thereof, thereby to secure said pin in said hole in said body;

said pin recess having a first depth into said pin and said wedging member being shorter in its height dimension into said recess than said first depth, whereby said wedging member is so shaped, with respect to the shape of said recess, that said wedging member applies force to spread said pin only at said pin free end.

* * * * *